United States Patent
Nogues Lopez et al.

(10) Patent No.: US 10,570,354 B2
(45) Date of Patent: Feb. 25, 2020

(54) FABRIC SOFTENER ACTIVE COMPOSITIONS

(71) Applicant: KAO Corporation S.A., Barbera del Valles (ES)

(72) Inventors: Blanca Nogues Lopez, Barbera del Valles (ES); Miquel Mundo Blanch, Barbera del Valles (ES); Carmen M. Pey Gutierrez, Barbera del Valles (ES); Jaume Sobrevias Alabau, Barbera del Valles (ES); Josep Vilaret Ferrer, Barbera del Valles (ES)

(73) Assignee: KAO Corporation S.A., Barbera del Valles (ES)

( * ) Notice: Subject to any disclaimer, the term of this patent is extended or adjusted under 35 U.S.C. 154(b) by 0 days.

(21) Appl. No.: 16/011,871

(22) Filed: Jun. 19, 2018

(65) Prior Publication Data

US 2018/0362885 A1    Dec. 20, 2018

(30) Foreign Application Priority Data

Jun. 20, 2017    (EP) .................................... 17382377

(51) Int. Cl.
| | | |
|---|---|---|
| C11D 1/62 | (2006.01) | |
| C11D 3/00 | (2006.01) | |
| C11D 3/30 | (2006.01) | |
| C11D 3/20 | (2006.01) | |
| C11D 11/04 | (2006.01) | |
| C11D 3/37 | (2006.01) | |
| C11D 3/50 | (2006.01) | |
| C07C 213/06 | (2006.01) | |
| C11D 1/645 | (2006.01) | |
| C07C 213/08 | (2006.01) | |
| C11D 11/00 | (2006.01) | |

(52) U.S. Cl.
CPC .......... C11D 3/0015 (2013.01); C07C 213/06 (2013.01); C07C 213/08 (2013.01); C11D 1/645 (2013.01); C11D 3/2013 (2013.01); C11D 3/2079 (2013.01); C11D 3/2093 (2013.01); C11D 3/30 (2013.01); C11D 3/37 (2013.01); C11D 3/50 (2013.01); C11D 11/0094 (2013.01); C11D 11/04 (2013.01); C11D 1/62 (2013.01)

(58) Field of Classification Search
CPC ....... C11D 3/2013; C11D 3/2079; C11D 1/62; C11D 3/2093; C11D 3/001; C11D 3/2006; C11D 7/262; C11D 1/10; C11D 7/266; C11D 3/33; C11D 9/267; C11D 1/52; C11D 3/30

See application file for complete search history.

(56) References Cited

U.S. PATENT DOCUMENTS

| | | | | |
|---|---|---|---|---|
| 4,464,273 A | * | 8/1984 | Parslow | C11D 1/62 510/524 |
| 4,830,771 A | | 5/1989 | Ruback et al. | |
| 5,422,021 A | | 6/1995 | Turner | |
| 6,465,419 B1 | | 10/2002 | Bermejo Oses et al. | |
| 2004/0048770 A1 | * | 3/2004 | Howard | C11D 1/835 510/515 |
| 2011/0245138 A1 | | 10/2011 | Kohle et al. | |
| 2013/0053299 A1 | * | 2/2013 | Kohle | C07C 213/06 510/521 |
| 2015/0159318 A1 | * | 6/2015 | Amatani | D06M 13/144 252/8.63 |

FOREIGN PATENT DOCUMENTS

| | | |
|---|---|---|
| EP | 0835863 A1 | 4/1998 |
| EP | 1239024 B1 | 11/2007 |
| EP | 2553066 B1 | 4/2014 |
| EP | 2553071 B1 | 5/2014 |
| EP | 2553067 B1 | 2/2015 |
| WO | 9419439 A1 | 1/1994 |
| WO | 2005001010 A1 | 1/2005 |
| WO | 2012072368 A1 | 6/2012 |
| WO | 2013126335 A1 | 8/2013 |

OTHER PUBLICATIONS

STIC Search Report dated Jul. 19, 2019.*
European Search Report dated Nov. 30, 2017 for priority document EP 17 38 2377.

* cited by examiner

Primary Examiner — Eisa B Elhilo
(74) Attorney, Agent, or Firm — Timothy J. Monahan; Monahan & Company, LLC

(57) ABSTRACT

The present invention relates to fabric softener active compositions comprising a combination of a mixture of quarternary ester ammonium compounds and fatty solvents (a fatty acid ester, a fatty acid, a fatty alcohol and mixtures thereof) and methods of making and using the same. The fabric softener active compositions preferably comprise component (a), said component being a mixture of quarternary ester ammonium compounds obtained by esterification of a mixture of alkanolamines comprises at least a trialkanolamine and a monoalkyldialkanolamine; component (b), said component being a fatty acid ester or a mixture of fatty acid esters, wherein the component (b) content is in the range from 5 to 60% wt. based on the total weight of the fabric softener active composition; and a component (c), said component being a fatty acid or a mixture of fatty acids, wherein the component (c) content is in the range from 0 to 15% wt. based on the total weight of the fabric softener active composition. The invention also proposes fabric softener compositions, comprising the previously described active compositions, and methods of making and using the same.

15 Claims, No Drawings

FABRIC SOFTENER ACTIVE COMPOSITIONS

FIELD OF THE INVENTION

The present invention relates to fabric softener active compositions comprising a combination of a mixture of quaternary ester ammonium compounds and fatty solvents (a fatty acid ester, a fatty acid, a fatty alcohol and mixtures thereof) and methods of making and using the same. The invention also proposes fabric softener compositions, comprising the previously described active compositions, and methods of making and using the same.

STATE OF THE ART

A fabric softener active composition has to meet several requirements, sometimes difficult to be met simultaneously, to be used in fabric softeners: i) high softening performance, ii) hydrolysis stability in aqueous dispersions with little change in dispersion viscosity, iii) suitable handling and processing in a liquid state, iv) good odour, v) appropriate compatibility with other components including perfumes, vi) ability to contribute to suitable viscosity profiles when to be used: a) in combination with other components of a softener composition and b) at the dilution.

Quaternary ester ammonium compounds commonly referred to as esterquats, have found broad use as fabric softener actives due to their high softening performance, their biodegradability and reasonably low aquatic toxicity.

Most of the commercially used quaternary ester ammonium compounds are solids. This makes their handling and processing in a pure state difficult: tendency to lump, high viscosity at low melt temperatures, unsatisfactory stability at higher melt temperatures. Use of these compounds in liquid fabric softeners is enhanced by converting them into molten compositions containing from 5 to 25% by weight of a solvent (addition of auxiliary substances is not excluded). The solvent function is to improve the quaternary ester ammonium compounds handling and processing (viscosity reduction in fabric softener active compositions and/or water dispersibility increase from the molten state), providing no benefits in terms of their softening performance though. Commonly used solvents such as ethanol or isopropanol are volatile and flammable substances. Such fabric softener active compositions have a low viscosity, but unfortunately, they have a low flash point of less than 60° C. and therefore require special safety measures when handling and processing and are subject to certain regulatory restrictions.

There are several attempts in the current state of the art aimed to overcome the drawbacks caused by the addition of the cited above flammable solvents.

WO2013126335 A1 proposes fabric softener active compositions which have reduced content of or no added solvents, can flow without having to heat them to very high temperatures that compromise the chemical stability of the product and are able to form stable, low-viscosity liquid fabric softeners. In one embodiment described therein, these fabric softener active compositions comprise at least one quaternary ester ammonium compound and less than 8% added solvent such as isopropanol. In the most preferred embodiment, the fabric softener active compositions contain no solvent. Examples 1-4 show synthesis of quaternary ester ammonium compounds with no solvent added to the reaction product. The viscosity of such fabric softener active compositions is less than 2000 cP at 80° C. They are reported as being easy to handle and process.

EP2553067 B1 discloses fabric softener active compositions having a low content of flammable solvents, a low melt viscosity and high stability in a molten state. These fabric softener active compositions comprise from 65 to 95% of a bis-(-2-hydroxyethyl)-dimethylammonium chloride fatty acid ester, from 2 to 8% of a fatty acid triglyceride (preferably a coconut oil or a hydrogenated coconut oil), and from 3 to 12% of a flammable alcohol selected from ethanol, 1-propanol and 2-propanol. The fabric softener active composition of Example 3 therein is prepared by mixing the powdered esterquat with coconut oil and 2-propanol at a percentage weight ratio of 88:4:8. Melt viscosities measured at 90° C. and at shear rates of 1, 10 and 100 $s^{-1}$ are 262, 236 and 194 cP, respectively. By contrast, melt viscosities of a fabric softener active composition of comparative example 2, consisting of the esterquat and coconut oil at a percentage weight ratio of 94:4, measured at conditions as defined above, are 13200, 9010 and 2290 cP, respectively.

EP2553066 B1 proposes fabric softener active compositions comprising at least 50% by weight of a bis-(2-hydroxypropyl)-dimethylammonium methylsulphate fatty acid ester (preferably from 85 to 95% by weight) and from 0.5 to 5% by weight of a fatty acid (preferably from 2 to 5% by weight). By adjusting the amount of fatty acid within this range, compositions of the present invention can be made which have low melt viscosities and good storage stability in aqueous dispersions without using any solvent or diluent. In spite of it, the fabric softener active compositions can comprise less than 10% by weight of solvent, having a flash point of less than 20° C. Additionally, they can comprise up to 9.9% by weight of at least one solvent selected from glycerol, ethylene glycol, propylene glycol, dipropylene glycol and C1-C4 alkyl monoethers of ethylene glycol, propylene glycol and dipropylene glycol. Moreover, they can further comprise from 2 to 8% by weight of a fatty acid triglyceride.

EP2553071 B1 discloses fabric softener active compositions having high softening performance and good storage stability in aqueous formulations to which they can be processed to without the use of volatile solvents. These compositions comprise at least 50% by weight of a bis-(2-hydroxypropyl)-dimethylammonium methylsulphate fatty acid ester, and from 0.5 to 5% by weight of a fatty acid. The fabric softener active compositions described therein comprise less than 10% by weight of a flammable solvent. In another preferred embodiment, the fabric softener active composition further comprises from 2 to 8% by weight a fatty acid triglyceride. The compositions obtained are reported to be heat stable.

EP1239024 B1 proposes softener compositions containing a quaternary ammonium salt used as a softener base agent. These softener compositions are reported to be excellent in softening properties, biodegradability and aquatic toxicity. They comprise a cationic surfactant comprising at least one selected from the group consisting of quaternized mono-esteramine (mono-esterquat), quaternized di-esteramine (di-esterquat), quaternized tri-esteramine (tri-esterquat), wherein the ratio of the tri-esterquat to the total amount of mono-esterquat, di-esterquat and tri-esterquat exceeds 50% and the ratio of mono-esterquat to the total amount of mono-esterquat, di-esterquat and tri-esterquat is not more than 10%. The softener compositions further comprise a non-ionic surfactant that is an alkoxylated (ethoxylated, propoxylated, butoxylated) fatty acid ester. Examples 7, 10-15 therein disclose use of ethoxylated hydrogenated tallow fatty acid methyl esters as quaternizing solvents so solutions of ethoxylated hydrogenated tallow fatty acid methyl ester adduct of quaternary ammonium salts are obtained. These solutions are further mixed with water to prepare softener compositions of characteristics as described above.

WO2005001010 A1 discloses a fabric softener compositions comprising a blend of quaternary ester ammonium compounds. Said blend is of methyldiethanolamine quaternary ester and of triethanolamine quaternary ester, wherein the content of mono alkyl ester quat of the methyldiethanolamine quaternary ester is of about 10% or greater. The fabric softener composition comprises a blend from 15 to 65% wt. of triethanolamine esterquat and from 35 to 85% wt. of methyldiethanolamine esterquat with high content of monoester. The compositions can further comprise aids to ensure stability, such as mono long chain alkyl cationic surfactants, alkoxylated non-ionic surfactants, amine oxides and fatty acids.

From the state of the art set forth above, it can be seen that there is still a need for fabric softener active compositions which are able to comply with the requirements imposed on them: i) high softening performance, ii) hydrolysis stability in aqueous dispersions with little change in dispersion viscosity, iii) suitable handling and processing in a liquid state, iv) good odour, and/or v) suitable compatibility with other components including perfumes. Furthermore, there is a need for an improved and more efficient method for obtaining fabric softener active composition comprising fewer steps.

The present invention aims, in particular, at the problem of providing fabric softener active in compositions showing low dropping points (preferably below 60° C.) in order to allow the handling in a molten state maximum 70° C., ensuring good chemical stability, while at the same time having good viscosity values at 70° C. so that they can be easily pumped in the molten state. Furthermore, the present invention aims at the further, alternative problem of providing fabric softener active compositions suitable viscosity with a low content or in the absence of flammable solvents. Finally, the present invention also aims at the further, alternative problem of providing fabric softener compositions with improved initial viscosity of their aqueous dispersions and/or improved softening performance properties.

Definitions

Fabric softener active composition: A composition comprising a component (a), a component (b), a component (c), and optionally a component (d).

Fabric softener composition: A composition comprising a fabric softener active composition comprising a component (a), a component (b), a component (c), and optionally a component (d), further comprising at least water, wherein the fabric softener active composition is present in an amount from 1 to 30% wt. based on the total weight of the fabric softener composition.

As used herein, the meaning of the term "comprising" encompasses three alternatives, namely "comprising", "consisting of" and "consisting essentially of".

SUMMARY OF THE INVENTION

The first object of the present invention is a fabric softener active composition comprising a component (a), a component (b), a component (c), and optionally a component (d).

A further object of the present invention is a method of preparation of a fabric softener active composition comprising a component (a), a component (b), a component (c), and optionally a component (d).

Another object of the present invention is a fabric softener composition comprising a fabric softener active composition that comprises a component (a), a component (b), a component (c), and optionally a component (d), further comprising at least water, wherein the fabric softener active composition is present in an amount from 1 to 30% wt. based on the total weight of the fabric softener composition.

A method of preparation of a fabric softener composition comprising a fabric softener active composition according to the invention is also an object of the present invention.

Another object of the present invention is a method for conditioning textiles or fabrics by providing a fabric softener composition comprising a fabric softener active composition according to the invention, contacting one more fabric articles with the fabric softener composition at one or more points during a laundering process, and allowing the fabric articles to dry or mechanically tumble-drying them.

DETAILED DESCRIPTION OF THE INVENTION

Fabric Softener Active Composition

The main object of the present invention is a fabric softener active composition comprising:
a component (a), said component comprising a mixture of at least a quaternary ester ammonium compound of formula (I) and at least a quaternary ester ammonium compound of formula (II):

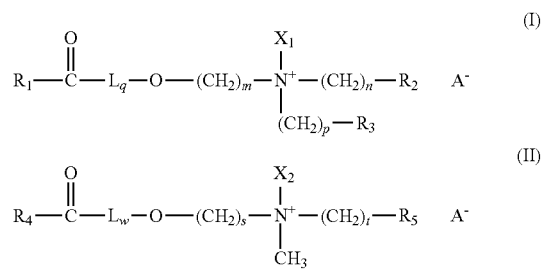

wherein in formula (I):
$X_1$ represents a hydroxyalkyl group containing 1 to 4 carbon atoms, an alkyl group containing 1 to 4 carbon atoms or an alkyl group containing one aromatic group;
$R_1$ is a linear or branched alkyl group containing 5 to 23 carbon atoms or a linear alkenyl group containing 5 to 23 carbon atoms and 1 to 3 double bonds;
$R_2$ and $R_3$ each independently represent —OH or —O-$L_q$-C(O)—$R_1$;
L represents a —$(OCH_2CH_2)_a$—$(OCHR_6CH_2)_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;
m, n and p each independently represent a number within the range from 1 to 4, q represents a number within the range from 0 to 26 and A represents an anion;
and wherein in formula (II):
$X_2$ represents a hydroxyalkyl group containing 1 to 4 carbon atoms, an alkyl group containing 1 to 4 carbon atoms or an alkyl group containing one aromatic group;
$R_4$ is a linear or branched alkyl group containing 5 to 23 carbon atoms or a linear alkenyl group containing 5 to 23 carbon atoms and 1 to 3 double bonds;

$R_5$ represents a —H, OH or —O-$L_w$-C(O)—$R_4$;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26:

s and t each independently represent a number within the range from 1 to 4, w represents a number within the range from 0 to 26 and A⁻ represents an anion;

a component (b), said component being a fatty acid t r or a nurture of fatty acid esters, wherein the component (b) content is in the range from 5 to 60% wt. based on the total weight of the fabric softener active composition;

a component (c), said component being a fatty acid or a mixture of fatty acids, wherein the component (c) content is higher than 0 and up to 15% wt, based on the total weight of the fabric softener active composition.

Preferably, the fabric softener active composition according to the present invention comprises:

a component (a), said component comprising a mixture of at least a quaternary ester ammonium compound of formula (I) and at least a quaternary ester ammonium compound of formula II:

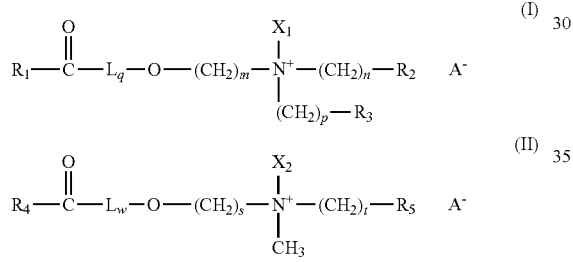

Wherein in formula (I):

$X_1$ represents a hydroxyalkyl group containing 1 to 4 carbon atoms, an alkyl group containing 1 to 4 carbon atoms or an alkyl group containing one aromatic group;

$R_1$ is a linear or branch d alkyl group containing 5 to 23 carbon atoms or a linear alkenyl group containing 5 to 23 carbon and 1 to 3 double bonds;

$R_2$ and $R_3$ each independently represent —OH or —O-$L_1$-C(O)—$R_1$;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20. b represents a number within the range of 0 to 6 and the sum of a+b represents the average alkoxylation degree which corresponds to a number within the range from 0 to 26;

m, n and p each independently represent a number within the range from 1 to 4, q represents a number within the range from 0 to 26 and A⁻ represents an anion;

and a wherein in formula (II):

$X_2$ represents a hydroxyalkyl group containing 1 to 4 carbon atoms, an alkyl group containing 1 to 4 carbon atoms or an alkyl group containing one aromatic group;

$R_4$ is a linear or branched alkyl group containing 5 to 23 carbon atoms or a linear alkenyl group containing 5 to 23 carbon atoms and 1 to 3 double bonds;

$R_5$ represents a —H, —OH or —O-$L_w$-C(O)—$R_4$;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and A⁻ represents an anion;

wherein the content of nitrogenated species in the fabric softener active composition is in the range from 40 to 95% wt., preferably in the range from 67 to 93% wt., based on the total weight of the fabric softener active composition;

a component (b), said component being a fatty acid ester or a mixture of fatty acid esters, wherein the component (b) content is in the range from 5 to 60% wt. based on the total weight of the fabric softener active composition, preferably from 5 to 40% wt., more preferably from 5 to 30% wt.;

a component (c), said component being a fatty acid or a mixture of fatty acids, wherein the component (c) content is higher than 0 and up to 15% wt. based on the total weight of the fabric softener active composition, preferably from 0.2 to 10% wt., more preferably from 0.2 to 3% wt.;

optionally a component (d), said component being a fatty alcohol or a mixture of fatty alcohols, wherein the component (d) content is in the range from 0 to 20% wt. based on the total weight of fabric softener active composition, preferably from 0 to 16% wt., more preferably from 0 to 12% wt.

More preferably, the fabric softener active composition according to the present invention comprises:

a component (a), said component comprising a mixture of at least a quaternary ester ammonium compound of formula (I) and at least a quaternary ester ammonium compound of formula II:

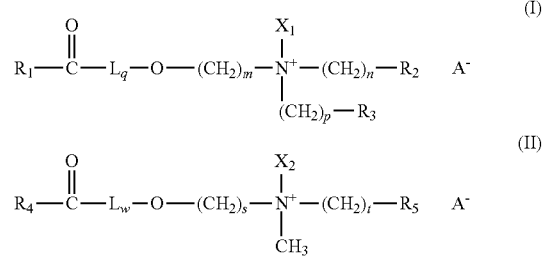

Wherein in formula (I):

$X_1$ represents a hydroxyalkyl group containing 1 to 4 carbon atoms, an alkyl group containing 1 to 4 carbon atoms or an alkyl group containing one aromatic group;

$R_1$ is a linear or branched alkyl group containing 5 to 23 carbon atoms or a linear alkenyl group containing 5 to 23 carbon atoms and 1 to 3 double bonds;

$R_2$ and $R_3$ each independently represent —OH or —O-$L_q$-C(O)—$R_1$;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

m, n and p each independently represent a number within the range from 1 to 4, q represents a number within the range from 0 to 26 and $A^-$ represents an anion;

and wherein in formula (II):

$X_2$ represents a hydroxyalkyl group containing 1 to 4 carbon atoms, an alkyl group containing 1 to 4 carbon atoms or an alkyl group containing one aromatic group;

$R_4$ is a linear or branched alkyl group containing 5 to 23 carbon atoms or a linear alkenyl group containing 5 to 23 carbon atoms and 1 to 3 double bonds;

$R_5$ represents a —H, —OH or —OLw-C(O)—R4;

L represents a —$(OCH_2CH_2)_a$—$(OCHR_6CH_2)_b$— group, wherein $R_6$ represents an alkyl group containing 1 to 4 carbon atoms, a represents a number within the range of 0 to 20, represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and $A^-$ represents an anion;

wherein the content of nitrogenated species in the fabric softener active composition is in the range from 40 to 95% wt. based on the total weight of the fabric softener active composition;

a component (b), said component being a fatty acid ester or a mixture of fatty acid esters, wherein the component (b) content is in the range from 5 to 60 wt. based on the total weight of the fabric softener active composition;

a component (c), said component being a fatty acid or a mixture of fatty acids, wherein the component (c) content is higher than 0 and up to 15% wt. based on the total weight of the fabric softener active composition.

a): Quaternary Ester Ammonium Compound;

The fabric softener active composition of the present invention comprises a component (a), said component comprising a mixture of at least a quaternary ester ammonium compound of formula (I) and at least a quaternary ester ammonium compound of formula (II):

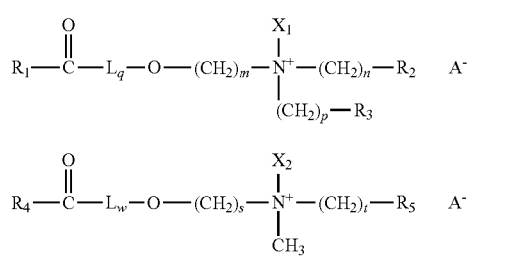

(I)

(II)

Wherein in formula (I):

$X_1$ represents a hydroxyalkyl group containing 1 to 4 carbon atoms, an alkyl group containing 1 to 4 carbon atoms or an alkyl group containing one aromatic group;

$R_1$ is a linear or branched alkyl group containing 5 to 23 carbon atoms or a linear alkenyl group containing 5 to 23 carbon atoms and 1 to 3 double bonds;

$R_2$ and $R_3$ each independently represent —OH or —O-$L_q$-C(O)—$R_1$;

L represents a —$(OCH_2CH_2)_a$—$(OCHR_6CH_2)_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

m, n and p each independently represent a number within the range from 1 to 4, q represents a number within the range from 0 to 26 and $A^-$ represents an anion;

and wherein in formula (II):

$X_2$ represents a hydroxyalkyl group containing 1 to 4 carbon atoms, an alkyl group containing 1 to 4 carbon atoms or an alkyl group containing one aromatic group;

$R_4$ is a linear or branched alkyl group containing 5 to 23 carbon atoms or a linear alkenyl group containing 5 to 23 carbon atoms and 1 to 3 double bonds;

$R_5$ represents a —H, OH or —O-Lw-C(O)—$R_4$;

L represents a —$(OCH_2CH_2)_a$—$(OCHR_6CH_2)_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and $A^-$ represents an anion;

In an embodiment of the present invention, the component (a), consists of a mixture of at least a quaternary ester ammonium compound of formula (I) and at least a quaternary ester ammonium compound of formula (II).

In an embodiment of the present invention, the mixture of at least a quaternary ester ammonium compound of formula (I) and at least a quaternary ester ammonium compound of formula II comprises at least one or more quaternary mono-, di- or tri-ester ammonium compounds (commonly known as mono-esterquat (mono-EQ), di-esterquat(di-EQ), tri-esterquat (tri-EQ)) of formula (I1), (I2), (I3), and at least one or more quaternary mono or di-ester ammonium compounds (also known as mono-esterquat (mono-EQ), di-esterquat (di-EQ)) of formula (II1), (II2), wherein the content of nitrogenated species in the fabric softener active composition is in the range from 40 to 95% wt. based on the total weight of the fabric softener active composition;

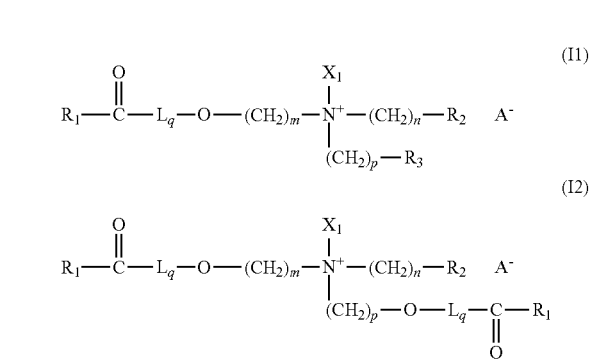

(II1)

(I2)

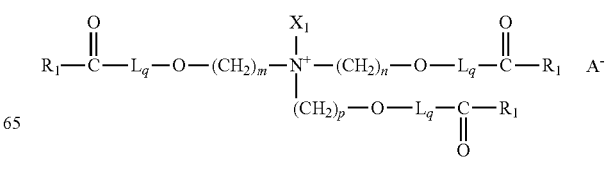

(I3)

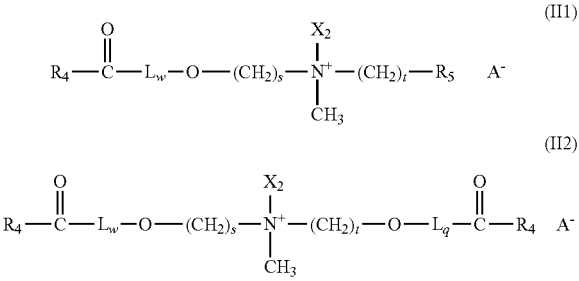

wherein in formulae (I1), (I2), (I3)

$R_2$ and $R_3$ each independently represent —OH;

$X_1$ represents a hydroxyalkyl group containing 1 to 4 carbon atoms, an alkyl group containing 1 to 4 carbon atoms or an alkyl group containing one aromatic group;

$R_1$ is a linear or branched alkyl containing 5 to 23 carbon atoms or a linear alkenyl group containing 5 to 23 carbon atoms and from 1 to 3 double bonds in formulae I1, I2 and I3 each $R_1$ can independently represent the same or different linear or branched alkyl chain;

$A^-$ represents an anion;

L represents a —$(OCH_2CH_2)_a$—$(OCHR_6CH_2)_b$— group, wherein $R_6$ represents an alkyl group containing 1 to 4 carbon atoms, a represents a number within the range of 0 to 20, b represents a number within the range of 0 to 6, and the sum of a+b represents the average alkoxylation degree which corresponds to a number from 0 to 26;

m, n, p each independently represents a number within the range from 1 to 4, q represents a number within the range from 0 to 26.

In a preferred embodiment m, n anal p ore equal to 2.

Also in a preferred embodiment, q represents an average number within the range of 0 to 10, more preferably within the range of 0 to 6, most preferred 0.

And wherein in formulae (II1), (II2)

$X_2$ represents a hydroxyalkyl group containing 1 to 4 carbon atoms, alkyl group containing 1 to 4 carbon atoms or an alkyl group containing one aromatic group;

$R_5$ represents —OH;

L represents a —$(OCH_2CH_2)_a$—$(OCHR_6CH_2)_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and $A^-$ represents an anion;

In a preferred embodiment s and t are equal to 2. Also in a preferred embodiment, q represents an average number within the range of 0 to 10, more preferably within the range of 0 to 6, most preferred 0.

The quaternary ester ammonium compounds of the invention can be ethoxylated and/or propoxylated, since a and b can be larger than 0. The order of sequence of the ethylene oxide and propylene oxide groups is not critical for the invention.

In the case q is 2 or larger, each L group may be the same or different. Also the Lq or Lw groups contained in the different branches within the compounds of formula (I1), (I2), (I3), (II1), (II2) may independently represent different meanings.

Preferably, $X_1$ and X2 are an alkyl group; more preferably $X_1$ and X2 are a methyl group.

Preferably, $A^-$ is selected from a halide, phosphate or alkylsulphate.

Within the present patent application, when a numerical range is indicated, all the individual numbers included in said range are intended to be included. The same shall apply to any other range indicated.

In a particularly preferred embodiment, the component (a) comprises a mixture of at least one quaternary mono-ester ammonium compound of formula (I1), at least one quaternary di-ester ammonium compound of formula (I2), and at least one quaternary tri-ester ammonium compound of formula (I3), wherein m=n=p=2; $R_1$—C(O)— is a linear acyl group wherein $R_1$ is a linear alkyl or a linear alkenyl containing from 11 to 21 carbon atoms, preferably derived from (hydrogenated and/or non-hydrogenated) tallow fatty acid or palm fatty acid; $R_2$ and $R_3$ each represent —OH, q is 0 (i.e. the compound is not alkoxylated); $X_1$ is a methyl group; and $A^-$ is selected from a halide, phosphate or alkylsulphate, preferably alkylsulphate and it also comprises at least one quaternary mono-ester ammonium compound of formula (II1) and at least one quaternary di-ester ammonium compound of formula (II2), wherein s=t=2; $R_4$—C(O)— is a linear acyl group wherein $R_4$ is a linear alkyl or a linear alkenyl containing from 11 to 21 carbon atoms, preferably derived from (hydrogenated and/or non-hydrogenated) tallow fatty acid or palm fatty acid; R5 represents —OH, w is 0 (i.e. the compound is not alkoxylated); X2 is a methyl group; and $A^-$ is selected from a halide, phosphate or alkylsulphate, preferably alkylsulphate.

In another embodiment of the present invention, the component (a) comprises a mixture of at least one or more quaternary mono-, di- or tri-ester ammonium compounds represented by formula (I1), (I2), (I3) as defined above, wherein $R_2$ and $R_3$ independently represent —OH; each m, n, p represents number 2 and at least one or more quaternary mono- or di-ester ammonium compound represented by formula (II1), (II2) as defined above, wherein R5 represents —OH, and a and t represent number 2.

The rest of variables have the meanings as indicated above for formula (I1), (I2), (I3), (II1), (II2).

In another embodiment of the present invention, $R_1$ is a linear or branched aryl containing 5 to 23 carbon atoms or a linear alkenyl group containing 5 to 23 carbon atoms and from 1 to 3 double bonds; preferably, the alkyl or alkenyl group contains from 11 to 21 carbon atoms.

In another embodiment of the present invention, $R_4$ is a linear or branched alkyl containing 5 to 23 carbon atoms or a linear alkenyl group containing 5 to 23 carbon atoms and from 1 to 3 double bonds; preferably, the alkyl or alkenyl group contains from 11 to 21 carbon atoms.

As used herein, the term "alkyl" refers to a straight or branched hydrocarbon chain containing from 1 to 23, preferably 5 to 23 carbon atoms.

As used herein, the term "alkenyl" refers to a linear hydrocarbon chain containing from 2 to 23, preferably 5 to 23 carbon atoms and from one to 3 unsaturations.

Linear or branched alkyl or linear alkenyl groups can originate from fatty acids, or methyl esters/triglycerides thereof, are alkyls or alkenyls derived from oils and fats from plants and animals, such as palm, palm kernel, coconut, rapeseed, sunflower, soybean, olive, canola, tall or tallow, possibly totally or partially hydrogenated and purified. Synthetic fatty acids, or methyl esters/triglycerides thereof, such as palmitoleic acid, oleic acid, elaidinic acid, petroselinic acid, linoleic acid, linolenic acid, stearic acid, myristic acid, gadoleic acid, behenic acid and erucic acid, or mixtures thereof, can also be employed in the present invention. Preferably, the linear or branched alkyl or linear alkenyl groups proceed from fatty acids derived from palm oil, coconut oil, tallow and hydrogenated tallow, more preferably from tallow or palm and hydrogenated tallow or palm.

The fatty acid is preferably a C11-C21 acid containing a degree of unsaturation such that the iodine value ("IV") is in the range from 0 to 100, preferably from 10 to 90, more preferably in the range from 15 to 85, most preferably 15 to 55.

The fatty acids employed in the present invention can have a cis to trans isomer ratio from 80:20 to 95:5. Preferably, the trans isomer content of said fatty acid is less than 10%.

As used herein, the term "alkyl group containing one aromatic group" refers the alkyl group as defined above, substituted by one aromatic group, wherein "aromatic group" refers to an aryl or heteroaryl group.

"Aryl" refers to aromatic ring systems comprising 6 to 14 carbon atoms, more particularly 6 to 10, even more particularly 6 carbon atoms. Examples of aryl groups are phenyl, naphthyl, indenyl, fenanthryl or anthracyl radical, preferably phenyl or naphthyl radical. Said aryl radical may be optionally substituted by one or more substituents such as hydroxy, mercapto, halo, phenyl, alkoxy, haloalkyl, nitro, cyano, dialkylamino, aminoalkyl, acyl and alkoxycarbonyl, as defined herein.

"Alkoxy" refers to an alkyl group as defined above bonded to an oxygen atom (R—O—).

Examples of halogen atoms are Br, Cl, I and F.

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. The heteroaryl group has 3 to 15 members and preferably 4 to 8 members, illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4) triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents such as hydroxy, mercapto, halo, alkyl, phenyl, alkoxy, haloalkyl, nitro, cyano, dialkylamino, aminoalkyl, acyl and alkoxycarbonyl, as defined herein. Preferably, a heteroaryl group is a monocyclic ring, wherein the ring comprises 2 to 5 carbon atoms and 1 to 3 heteroatoms.

In another embodiment of the present invention, the linear or branched alkyl containing 5 to 23 carbon atoms or a linear alkenyl group containing 5 to 23 carbon atoms and from 1 to 3 double bonds as defined above for $R_1$ and $R_4$ are derived from the same fatty acid.

Preparation of Quaternary Ester Ammonium Compound:

The component (a) comprises a mixture of at least a quarternary ester ammonium compound of formula (I) and at least a quaternary ester ammonium compound of formula (II) according to the invention. The component (a) can be prepared by i) esterification, reacting a fat source, preferably a fatty acid or a methyl ester/triglyceride thereof, with a mixture of alkanotamines (for example, but not limited to, triethanolamine, methyldiethanolamine or dimethylethanolamine) to obtain a mixture containing esteramine, and ii) subsequently quaternizing the mixture with an alkylating agent.

In an embodiment of the present invention, the mixtures of alkanolamines comprise at least a trialkanolamine and at least an alkylalkanolamine.

In an embodiment of the present invention, the trialkanolamine has the following formula (III)

$$N\text{—}[(CH_2)_v\text{—}OH]_3 \quad (III)$$

Wherein v represents a number within the range from 1 to 5, more preferably 1 to 3, most preferred is 2.

In another embodiment of the present invention, the alkylkanolamine has the following formula (IV)

$$(R_7)_x\text{—}N\text{—}[(CH_2)y\text{-}OH]_{3-x} \quad (IV)$$

Wherein $R_7$ represents an alkyl group containing 1 to 4 C atoms, x represents a number within the range from 1 to 2.

In an embodiment of the present invention, the alkylalkanolamine preferably is a monoalkyldialkanolamine, wherein X=1 and y=2.

In an embodiment of the present invention, the mixture of alkanolamines comprises at least a trialkanolamine and a monoalkyldialkanolamine. In a most preferred embodiment of the present invention, the mixture of alkanolamines comprises at least a triethanolamine (TEA) and a methyldiethanolamine (MDEA).

In another embodiment of the present invention, the weight ratio between the trialkanolamine and the monoalkyldialkanolamine used as the starting materials for preparing component (a) is in the range between 99/1 to 1/99, preferably between 95/5 to 30/70, even more preferably between 90/10 to 50/50.

I) Esterification Step:

It is preferred that the fat source employed in the esterification step is a fatty acid or a mixture of fatty acids. In case a fatty acid methyl ester or a fatty acid triglyceride is used, the transesterification conditions are those described in the state of the art.

The reaction between the fatty acid and the mixture of alkanolamines is an esterification which leads to the formation of an esteramine or a mixture of esteramines, and it may be conducted in a known way, as described for example in document ES-A-2021900. Preferably the esterification reaction is carried out at temperature between 150 and 200° C., for a period of 2-10 hours, preferably at a reduced pressure of about 5 to 200 mbar and in the presence of one of the catalysts known for the esterification, such as hypophosphorous acid or paratoluenesulfonic acid, and also in the presence of any of the usual stabilizers and antioxidants such as tocopherols, BHT, BHA, etc.

In an embodiment of the present invention, a pre-mixture of alkanolamines that react with the fatty acid is prepared prior to the esterification step.

In an embodiment of the present invention, the mixture of alkanolamines that react with the fatty acid comprises at least a triethanolamine and at least a methyldiethanolamine.

In another embodiment of the present invention, the weight ratio between the triethanolamine and the methyldiethanolamine is in the range 99/1 to 1/99, preferably 95/5 to 30/70, even more preferably 90/10 to 50/50.

In an embodiment of the present invention, a fatty alcohol or a mixture of fatty alcohols is additionally added to the system in the esterification step. A part of the fatty acid present in the system may react with a fatty alcohol resulting in a fatty acid fatty alcohol ester, as a further product of the esterification step, formed in addition to the esteramine/s. Suitable fatty alcohol is a $C_6$-$C_{24}$ alcohol or alkoxylated alcohol, or polyol, preferably a $C_{12}$-$C_{18}$ alcohol.

The molar ratio of fatty acid to alkanolamine is from 1.4:1 to 2.5:1, preferably from 1.6:1 to 2.2:1.

The product resulting from the esterification reaction comprises a mixture of at least one or more mono-, di- and tri-esters of fatty acids and trialkanolamine and at least one or more mono- and di-esters of fatty acids and alkylalkanolamine. The product may also contain free trialkanolamine, free alkylalkanolamine, free fatty acid and free fatty alcohol. The progress of the reaction may be monitored by non-aqueous potentiometric titration with KOH.

ii) Quaternization Step:

The quaternization of the esterification reaction product of alkanolamines with the fatty acid is conducted in a known way, as described for example in WO-A-9101295. Preferred alkylating agents include, but are not limited to, methyl chloride, dimethyl sulphate or mixtures thereof.

The quaternization may take place in bulk or in solvent, at temperatures ranging from 40 to 90° C. If an added solvent is employed, then the starting materials and/or product must be soluble in the solvent to the extent necessary for the reaction (possible solvents can be the same solvents as used as component (b), component (c) and component (d) as defined below).

The composition that results from the quaternization process comprises a mixture of quaternized ester compounds having one (monoesterquat), two (diesterquat) or three (triesterquat) ester groups derived from the esterification of fatty acid with a trialkanolamine and it also comprises quaternized ester compounds having one (monoesterquat) or two (diesterquat) ester groups derived from the esterification of fatty acid with alkylalkanolamine. The product may also contain quaternized alkanolamine, unreacted esteramine, unreacted fatty acid, as well a fatty acid alkyl ester, preferably a fatty acid methyl ester or a fatty acid ethyl ester.

In an embodiment of the present invention, the content of fatty acid alkyl ester, preferably a fatty acid methyl ester or a fatty acid ethyl ester is in the range from 0 to 5% wt. based on the total weight of the fabric softener active composition, preferably in the range from 0 to 3% wt. based on the total weight of the fabric softener active composition, more preferably in the range from 0 to 2% wt. based on the total weight of the fabric softener active composition.

In an embodiment of the present invention, the component (a), said component comprising a mixture of at least a quaternary ester ammonium compound of formula (I) and at least a quaternary ester ammonium compound of formula (II) is obtained from an esteramine mixture obtained by esterification of a mixture of triethanolamine and methyldiethanolamine and tallow and/or hydrogenated tallow fatty acid and/or palm fatty acid followed by quaternization.

In another embodiment of the present invention, the component (a), said component comprising a mixture of at least one or more quaternary mono-, di- or tri-ester ammonium compounds of formula (I1), (I2), (I3) and one or more quaternary mono- or di-ester ammonium compounds of formula (II1), (II2) is obtained from an esteramine mixture obtained by esterification of a mixture of triethanolamine and methyldiethanolamine and tallow and/or hydrogenated tallow fatty acid and/or palm fatty acid followed by quaternization.

In another embodiment of the present invention, the component (a), said component comprising a mixture of at least one or more quaternary mono-, di- or ti-ester ammonium compounds of formula (I1), (I2), (I3) and one or more quaternary mono- or di-ester ammonium compounds of formula (II1), (II2) is obtained from an esteramine mixture obtained by esterification of a mixture of triethanolamine and methyldiethanolamine, and tallow and/or hydrogenated tallow fatty acid and/or palm fatty acid followed by quaternization, wherein the weight ratio between triethanolamine and methyldiethanolamine is in the range between 90/10 to 50/50.

The quaternization reaction may take place in a degree from 60 to 95% of the totality of the reaction.

Preparation of the component (a) is carried out under conditions according to the person skilled in the art to obtain a mixture of at least one or more quaternary mono-, di- or tri-ester ammonium compounds of formula (I1), (I2), (I3) and at least one or more quaternary mono-, or di-ester ammonium compounds of formula (II1), (II2).

In an embodiment of the present invention, the component (a) comprises a mixture of at least one or more quaternary mono-, di- or tri-ester ammonium compounds of formula (I1), (I2), (I3), wherein m=n=p; $R_1$—C(O)— is a linear acyl group wherein $R_1$ is an alkyl or alkenyl group containing from 11 to 21 carbon atoms, preferably derived from (hydrogenated or non-hydrogenated) tallow fatty acid or palm fatty acid; $R_2$ and $R_3$ each represent —OH, q is 0 (i.e. the compound is not ethoxylated); $X_1$ is a methyl group; and $A^-$ is selected from a halide, phosphate or alkylsulphate, preferably alkylsulphate and at least one or more quaternary mono- or di-ester ammonium compounds of formula (II1), (II2), wherein s=t=2; R4-C(O)— is a linear acyl group wherein R4 is a linear alkyl or a linear alkenyl containing, from 11 to 21 carbon atoms, preferably derived from (hydrogenated and/or non-hydrogenated) tallow fatty acid or palm fatty acid; R5 represents —OH, w is 0 (i.e. the compound is not alkoxylated): X2 is a methyl group; and $A^-$ is selected from a halide, phosphate or alkylsulphate, preferably alkylsulphate.

Such compound may be produced by esterifying (hydrogenated and/or non-hydrogenated) tallow fatty acid or palm fatty acid and a mixture of triethanolamine and methyldiethanolamine, wherein the ratio of triethanolamine to methyldiethanolamine is from 99/1 to 1/99, preferably between 95/5 to 30/70, even more preferably between 90/10 to 50/50, and wherein the ratio of tallow fatty acid or palm fatty acid to the mixture of triethanolamine and methyldiethanolamine is from 1.6:1 to 2.2:1, and subsequently methylating the esteramine obtained thereby.

(b): Fatty Acid Ester

The fabric softener active composition of the present invention comprises a component b), said component being a fatty acid ester or a mixture of fatty acid esters, wherein the component (b) content is in the range from 5 to 60% wt. based on the total weight of the fabric softener active composition, preferably from 5 to 40% wt., more preferably from 5 to 30% wt., and even more preferably from 12.7 to 14.0% wt The component (b) present in the fabric softener active composition is intentionally added in the esterification step, after the esterification step, in the quaternization step, or after the quaternization step and/or generated in situ in the esterification step or in the quaternization step.

In another embodiment of the present invention, the component (b) present in the fabric softener active composition is obtained in the esterification step by the reaction between the fatty acid or the mixture of fatty acids and a fatty alcohol or a mixture of fatty alcohols additionally added into the system.

In another embodiment of the present invention, the component (b) present in the fabric softener active composition is added to the system after the esterification step has finished, and can act as a solvent for the quaternization step.

In another embodiment of the present invention, the component (b) present in the fabric softener active composition is added to the component (a) after the quaternization step as an additive.

Yet in another embodiment of the present invention, the component (b) present in the fabric softener active composition corresponds to the combination of the previously described embodiments.

In one preferred embodiment of the invention, the component (b) has the following formula (4):

wherein
- $R_8$ represents a fatty acid moiety being a linear or branched alkyl containing 5 to 23 carbon atoms or a linear alkenyl group containing 5 to 23 carbon atoms and from 1 to 3 double bonds. Preferably, the alkyl or alkenyl group contains from 11 to 21 carbon atoms. Preferably, the alkyl or alkenyl group proceeds from fatty acids derived from palm oil, coconut oil, tallow and hydrogenated tallow, more preferably from tallow or palm and hydrogenated tallow or palm.
- $R_9$ represents an alkyl or alkenyl group derived from a linear or branched, possibly alkoxylated (ethoxylated, propoxylated, butoxylated), alcohol containing 1 to 24 carbon atoms, preferably represents an alcohol containing 12 to 18 carbon atoms.

In another embodiment of the present invention, the component (b) is derived from: i) polyols, such as glycerol, sorbitol, pentaerythritol, etc. or ii) low or polymeric glycols, such as ethylene glycol, propylene glycol, dipropylene glycol, polyethylene glycol, polypropylene glycol, etc.

In another embodiment of the present invention, the fatty acid moieties in the component (b) and the component (a) are derived from the same fatty acid or mixture of fatty acids.

In another embodiment of the present invention, the component (b) is a fatty acid ester or a mixture of fatty acid esters derived from a $C_{12}$-$C_{18}$ fatty alcohol or a mixture of $C_{12}$-$C_{18}$ fatty alcohols.

In another embodiment of the present invention, the alkyl or alkenyl group resulting from a linear or branched, possibly alkoxylate (ethoxylated, propoxylated, butoxylated), alcohol containing 1 to 24 carbon atoms in component (b) is derived from a $C_{12-18}$ fatty alcohol or a mixture of $C_{12}$-$C_{18}$ fatty alcohols.

(c): Fatty Acid

The fabric softener active composition of the present invention comprises a component c, said component being a fatty acid or a mixture of fatty acids, herein, the component (c) is higher than 0 and up to 15% wt. based on the total weight of the fabric softener active composition, preferably from 0.2 to 10% wt, more preferably from 0.2 to 3% wt., and further preferably from 0 to 0.8% wt. and/or from 0.8 to 0.9% wt.

The component (c) present in the fabric softener active composition is intentionally added in the esterification step, after the esterification step, in the quaternization step, or after the quaternization step and/or accounts for an unreacted material.

In one embodiment of the present invention, the component (c) present in the fabric softener active composition corresponds to a free or unreacted fatty acid obtained after the esterification step which has not reacted with alkylating agent in the quaternization step to form a fatty acid methyl ester.

In another embodiment of the present invention, the component (c) present in the fabric softener active composition corresponds to a fatty acid or a mixture of fatty acids added to the esterification product, before the quaternization step, and which has not reacted with alkylating agent in the quaternization step to result in a fatty acid methyl ester.

In another embodiment of the present invention, the component (c) present in the fabric softener active composition is added to the component (a) after the quaternization step as an additive.

Yet in another embodiment of the present invention, the component (c) present in the fabric softener active composition corresponds to the combination of the previously described embodiments.

Suitable $C_6$-$C_{22}$ fatty acids are those obtained from vegetable and animal oils and fats such those obtained from castor oil, coconut oil, corn oil, mustard oil, olive oil, palm oil, peanut oil, rapeseed oil, sunflower oil, soybean oil, tall oil, tallow, eventually totally or partially hydrogenated, as well as purified or synthetic fatty acids, like caproic acid, caprylic acid, capric acid, isotridecanoic acid, lauric acid, myristic acid, palmitic acid, palmoleic acid, stearic acid, isostearic acid, 2-ethythexanoic acid, oleic acid, elaidinic acid, petroselenic acid, linoleic acid, linolenic acid, eleostearic acid, ricinoleic acid, arachidic acid, gadoleic acid, behenic acid, erucic acid, or their technical-grade mixtures.

In another embodiment of the present invention, the component (c) is a $C_{12}$-$C_{20}$ fatty acid or a mixture of $C_{12}$-$C_{20}$ fatty acids In another embodiment of the present invention, the component (c) and the component (a) are derived from the same fatty acid or mixture of fatty acids.

The fatty add is preferably a $C_{12}$-$C_{20}$ acid containing a degree of unsaturation such that the iodine value ("IV") is in the range 0-90, preferably 10-90, more preferably in the range 15-85, most preferably 15-55.

d): Fatty Alcohol

The fabric softener active composition of the present invention optionally comprises a component (d), said component being a fatty alcohol or a mixture of fatty alcohols, wherein the component (d) content is in the range from 0 to 20% wt. based on the total weight of the fabric softener active composition, preferably from 0 to 16% wt., more preferably from 0 to 12% wt., further preferably from 2.6 to 3.8% wt.

The component (d) present in the fabric softener active composition is intentionally added in the esterification step, after the esterification step, in the quaternization step, or after the quaternization step and/or accounts for an unreacted material.

In one embodiment of the present invention, the component (d) present in the fabric softener active composition corresponds to a free or unreacted fatty alcohol that has not reacted with a fatty acid in the esterification step to form a fatty acid fatty alcohol ester.

In another embodiment of the present invention, the component (d) present in the fabric softener active composition corresponds to a fatty alcohol or a mixture of fatty alcohols added to the esterification product as a quaternizing solvent.

In another embodiment of the present invention, the component (d) present in the fabric softener active composition is added to the component (a) after the quaternization step as an additive.

Yet in another embodiment of the present invention, the component (d) present in the fabric softener active composition corresponds to the combination of the previously described embodiments.

In another embodiment of the present invention, the fabric softener active composition comprises essentially no component (d).

Suitable fatty alcohol is a $C_6$-$C_{24}$ alcohol r alkoxylated (ethoxylated, propoxylated, butoxylated) alcohol, or polyol, preferably a $C_{12}$-$C_{18}$ alcohol.

The fabric softener active composition according to the present invention may contain further components.

(e): Solvent

The present invention may further comprise a component (a), said component being a solvent. In a preferred embodiment, the component (e) content is 0 or higher and lower than 8% wt. based on the total weight of the fabric softener active composition, preferably 0 or higher and lower than 6% wt., more preferably 0 or higher and lower than 5% wt.

In the most preferred embodiment, the fabric softener active composition comprises essentially no solvent. The fabric softener active composition does not require the presence of a solvent to comply with the purpose of the invention.

Solvents useful in the present technology include flammable liquids of flash point equal to or lower than 40° C. selected from the following list: methanol, ethanol, 1-propanol, 2-propanol, 1-butanol, 2-butanol, hexane, heptane, and combinations thereof. Preferably, the solvent is ethanol or 2-propanol and most preferably 2-propanol.

Other suitable solvents for use in the present invention include ethylene glycol, trimethylene glycol, tetramethylene glycol, pentamethylene glycol, hexamethylene glycol, diethylene glycol, triethylene glycol, propylene glycol, dipropylene glycol and C1-C4 alkyl monoethers of ethylene glycol, propylene glycol, and dipropylene glycol, sorbitol, alkane diols such as 1,2-propanediol, 1,3-propanediol, 2,3-butanediol, 1,4-butanediol, 1,3-butanediol, 1,5-pentanediol, and 1,6 hexanediol, phenylethyl alcohol, 2-methyl-1,3-propanediol, hexylene glycol, sorbitol, polyethylene glycols, 1,2-hexanediol, 1,2-pentanediol, 1,2-butanediol, 1,4-cyclohexanedimethanol, pinacol, 2,4-dimethyl-2,4-pentanediol, 2,2,4-trimethyl-I,3-pentanediol (and ethoxylates), 2-ethyl-I,3-hexanediol, phenoxyethanol (and ethoxylates), glycol ethers, butyl carbitol, dipropylene glycol n-butyl ether, or combinations thereof.

A method to obtain a fabric softener active composition according to the present invention comprises:
  i) an esterification step, wherein a fatty acid, a methyl ester or a triglyceride thereof is reacted with a mixture of alkanolamines to obtain a mixture containing an esteramine; and
  ii) a quaternization step, wherein the mixture obtained after the esterification step is reacted with an alkylating agent.

Preferably, a $C_{16}$-$C_{20}$ fatty alcohol is added in the esterification step, after the esterification step, in the quaternization step or after the quaternization step. Even more preferably, a fatty acid, a methyl ester or a triglyceride thereof is added in the quaternization step or after the quaternization step.

The term "added in the esterification/quaternization step" as used herein refers to addition of the respective component to the esterification/quaternization reaction mixture either prior to or in course of the esterification/quaternization reaction.

The method to obtain a fabric softener active composition according to the present invention is characterized in that the component (b) present in the fabric softener active composition is intentionally added in the esterification step, after the esterification step, in the quaternization step or after the quaternization step and/or generated in situ in the esterification step or in the quaternization step. Preferably, the method to obtain a fabric softener active composition according to the present invention may be further characterized in that the component (c) present in the fabric softener active composition is intentionally added in the esterification step, after the esterification step, in the quaternization step or after the quaternization step and/or corresponds to an unreacted material. Even more preferably, the method to obtain a fabric softener active composition according to the present invention may be further characterized in that the component (d) present in the fabric softener active composition is intentionally added in the esterification step, after the esterification step, in the quaternization step or after the quaternization step and/or corresponds to an unreacted material.

Preferably, the fabric softener active composition of the present invention comprises
  a component (a), said component comprising a mixture of at least a quaternary ester ammonium compound of formula (I) and at least a quaternary ester ammonium compound of formula (II), wherein the content of nitrogenated species in the fabric softener active composition is in the range from 40 to 95% wt. based on the total weight of the fabric softener active composition;
  a component (b), said component being a fatty acid ester or a mixture of fatty acid esters, wherein the component (b) content is in the range from 5 to 60% wt, based on the total weight of the fabric softener active composition, preferably from 5 to 40% wt., more preferably from 5 to 30% wt.;
  a component (c), said component being a fatty acid or a mixture of fatty acids, wherein the component (c) content is higher than 0 and up to 15% wt. based on the total weight of the fabric softener active composition, preferably from 0.2 to 10% wt., more preferably from 0.2 to 3% wt:
  a component (d), said component being a fatty alcohol or a mixture of fatty alcohols, wherein the component (d) content is in the range from 0 to 20% wt. based on the total weight of the fabric softener active composition, preferably from 0 to 16% wt, more preferably from 0 to 12% wt.

In an embodiment of the present invention, the fabric softener active composition of the present invention comprises:
  a component (a), said component comprising a mixture of at least one or more quaternary mono-, di- or tri-ester ammonium compounds of formula (I1), (I2), (I3) and at least one or more quaternary mono- or di-ester ammonium compounds of formula (II1), (II2), wherein the content of nitrogenated species in the fabric softener active composition is in the range from 65 to 95% wt. based on the total weight of the fabric softener active composition;
  a component (b), said component being a fatty acid ester or a mixture of fatty acid esters, wherein the component (b) content is in the range from 5 to 30% wt. based on the total weight of the fabric softener active composition, preferably from to 8 to 30% wt., more preferably from 12 to 30% wt.;

a component (c), said component being a fatty add or a mixture of fatty adds, wherein the component (c) content is in the range from 0.5 to 15% wt. based on the total weight of the fabric softener active composition, preferably from 1 to 15% wt., more preferably from 2 to 15% wt.;

a component (d), said component being a fatty alcohol or a mixture of fatty alcohols, wherein the component (d) content is in the range from 0 to 20% wt. based on the total weight of the fabric softener composition, preferably from 2 to 10% wt., more preferably from 2 to 5% wt.

n one embodiment of the present invention, the component (a) comprises at least one quaternary mono-ester ammonium compound of formula (I1), at least one quaternary di-ester ammonium compound of formula (I2), and at least one quaternary tri-ester ammonium compound of formula (I3), wherein m=n=p=2; $R_1$—C(O)— is a linear acyl group wherein $R_1$ is a linear alkyl or alkenyl containing from 11 to 21 carbon atoms, preferably derived from (hydrogenated or non-hydrogenated) tallow fatty acid or palm fatty acid; $R_2$ and $R_3$ each represent —OH, q is 0 (i.e. the compound is not alkoxylated); $X_1$, is a methyl group; and $A^-$ is selected from a halide, phosphate or alkylsulphate, preferably alkylsulphate and it also comprises at least one quaternary mono-ester ammonium compound of formula (II1) and at least one quaternary di-ester ammonium compound of formula (II2), wherein s=t=2; $R_4$—C(O)— is a linear acyl group wherein R4 is a linear alkyl or a linear alkenyl containing from 11 to 21 carbon atoms, preferably derived from (hydrogenated and/or non-hydrogenated) tallow fatty acid or palm fatty acid; R5 represents —OH and R6 represents —H, w is 0 (i.e. the compound is not alkoxylated); X1 is a methyl group; and $A^-$ is selected from a halide, phosphate or alkylsulphate, preferably alkylsulphate. Such a compound may be produced by esterifying tallow fatty acid and a mixture of triethanolamine and methyldiethanolamine, wherein the weight ratio between triethanolamine and methyldiethanolamine is in the range between 90/10 to 50/50; wherein the molar ratio of tallow fatty acid to alkanolamine is 1.4-2.5, preferably 1.6-2.2, and subsequently methylating the esteramine obtained thereby, wherein the degree of quaternization is from 25 to 95%.

In anti embodiment of the present invention, the component (b) is a $C_{12-18}$ fatty acid ester, wherein the fatty acid source is preferably palm oil, coconut oil, tallow and hydrogenated tallow, more preferably palm oil and/or tallow and hydrogenated tallow.

In another embodiment of the present invention, the component (c) is preferably a $C_{12}$-$C_{20}$ fatty acid containing a degree of unsaturation such that the iodine value ("IV") is in the range 15-55.

In another embodiment of the present invention, the component (d) is $C_{12-18}$ fatty alcohol.

In another embodiment of the present invention, the fabric softener active composition further comprises a component (e), said component being a solvent, wherein the solvent content is higher than 0% and lower than 8% wt. based on the total weight of the fabric softener active composition, preferably lower than 6% wt., more preferably lower than 5% wt.

In another embodiment of the present invention, the component (e) is chosen from ethanol, 1-propanol and 2-propanol. The component (d) is preferably ethanol or 2-propanol and most preferably 2-propanol.

Yet in another embodiment of the present invention, the component (e) can further comprise glycols, preferably propylene glycol.

In an embodiment of the present invention, the fabric softener active composition comprises, in the indicated amounts expressed as percentage by weight with respect to the total weight of the composition:
a component a) comprising at least a mixture of one or more quaternary ester ammonium compound of formula (I) and one or more quaternary ester ammonium compounds of formula (II),
5 to 50% of the component b),
0.5 to 15% of the component c),
0 to 20% of the component d).

In another embodiment of the invention, the fabric softener active composition comprises, in the indicated amounts expressed as percentage by weight with respect to the total weight of the composition:
A component a) comprising at least a mixture of one or more quaternary ester ammonium compounds of formula (I) and one or more quaternary ester ammonium compounds of formula (II),
5 to 50% of the component b),
0.5 to 15% of the component c),
0 to 20% of the component d),
0 to 8% of the component e).

In a particularly preferred embodiment of the present invention, the fabric softener active composition comprises no component (e).

In another embodiment of the present invention, the sum content of the component (a), the component (b) and the component (c) is in the range from 5 to 80% wt. based on the total weight of the fabric softener active composition, more preferably from 10 to 60% wt., Additionally, the weight ratio (b)/(c) of the component (b) and the component (c) is equal to or higher than 45/55, preferably in the range from 45/55 to 99.5/0.5, whereas the weight ratio (b)/(d) of the component (b) and the component (d) is in the range from 50/50 to 95/5.

In an embodiment of the present invention, the fabric softener active composition consists of components (a), (b) and (c). In another embodiment of the present invention, the fabric softener active composition consists of components (a), (b), (c) and (d). In another embodiment of the present invention, the fabric softener active composition consists of components (a), (b), (c) and (e). In another embodiment of the present invention, the fabric softener active composition consists of components (a), (b), (c), (d) and (e).

In embodiment of the present invention, the fabric softener active composition contains from 65 to 95% wt., more preferably from 67 to 93% wt. of nitrogenated species based on the total weight of the fabric softener active composition.

The fabric softener active composition can be used to soften fabrics by treating the fabric with the composition. This can be done in a dryer when using a dryer sheet impregnated with the fabric softening active composition.

Fabric Softener Composition

Another of the present invention is a fabric softener composition comprising a fabric softener active composition that comprises a component (a), a component (b), a component (c), and optionally a component (d), further comprising at least water, wherein the fabric softener active composition is present in an amount from 1 to 30% wt. based on the total weight of the fabric softener composition, more preferably from 1.5 to 25% wt., most preferably from 2 to 20% wt.

In one embodiment of the present invention, the fabric softener composition further comprises optional components. In referring to the optional components, without this having to be regarded as an exhaustive description of all possibilities, which, on the other hand, are well known to the person skilled in the art, the following may be mentioned:

a) other products that enhance the performance of the softener compositions, such as silicones, amine oxides, anionic surfactants, such as lauryl ether sulphate or lauryl sulphate, amphoteric surfactants, such as cocoamidopropyl betaine or alkyl betaines, sulphosuccinates, polyglucoside derivatives, etc.

stabilising products, such as salts of amines having a short chain, which are quaternized or non-quaternized, for example of triethanolamine, N-methyldiethanolamine, etc., and also non-ionic surfactants, such as ethoxylated fatty alcohols, ethoxylated fatty amines.

c) products that improve viscosity control, such as inorganic salts, for example, calcium chloride, magnesium chloride, calcium sulphate, sodium chloride etc.; products which can be used to reduce viscosity in concentrated compositions, such as compounds of the glycol type, for example, ethylene glycol, dipropylene glycol, polyglycols, etc.; thickening agents for diluted compositions, such as polymers, suitable polymers are water soluble or dispersible, preferably the polymers are cationic. Suitable cationic polymeric materials include cationic guar polymers, cationic cellulose derivatives, cationic potato starch, and cationic polyacrylamides. Specially suitable are cross-linked water swellable cationic polymers. Those described polymers may also act as deposition aids.

d) components for adjusting the pH, which is from 2.0 to 6.0, preferably from 2.5 to 4.0, such as any type of inorganic and/or organic acid, for example hydrochloric, sulphuric, phosphoric, citric acid etc.

e) agents that improve soil release, such as the known polymers or copolymers based on terephthalates.

f) preservatives, such as bactericides, for example, 1,2-benzisothiazolin-3-one, 5-chloro-2-methyl-4-isothiazolin-3-one and 2-methyl-4-isothiazolin-3-one, or their combinations, 2-bromo-2-nitropropane-1,3-diol, etc.

g) other products such as antioxidants, colouring agents, perfumes, germicides, fungicides, anti-corrosive agents, anti-crease agents, opacifiers, optical brighteners, pearl lustre agents, etc.

In a preferred embodiment of the present invention, the fabric softener composition comprises a perfume or perfume microcapsule, wherein the perfume content is lower than 5% wt. based on the total weight of the fabric softener composition, preferably lower than 3% wt., more preferably lower than 2% wt.

In a particularly preferred embodiment of the present invention, the fabric softener composition comprises:

a) from 0 to 2% of an electrolyte concentration aid, preferably from 0.01 to 1%, more preferably from 0.02 to 0.5%; and/or b) from 0.01 to 3% of a thickening polymer, preferably from 0.02 to 1%, more preferably from 0.05 to 0.5%; and/or c) from 0.01 to 5% of a perfume, alternatively from 0.1 to 4% or from 0.2 to 4% of a neat perfume and optionally from 0.01 to 3%, preferably from 0.1 to 2%, more preferably from 0.3 to 1%, of a perfume microcapsule.

Preparation of Fabric Softener Composition

The fabric softener composition of the present invention can be obtained following a conventional process of mixing the different components, well known by any skilled person. For example, the different components can be mixed in the molten state, added to the water and stirred to obtain a homogeneous dispersion and then cooled down. In a preferred process of obtention, electrolytes and/or polymers, if present in the composition, are added to the water previous to the dispersion of the fabric softener active composition, or once the fabric softener active composition is dispersed in water. Perfume is preferably added once the blend is cooled down.

Method for Conditioning Textiles

The fabric softener composition according to the invention can be used in both a so-called non-rinse and a so-called rinse process, where a fabric softener composition as defined above is first diluted in an aqueous rinse bath solution. Subsequently, the laundered fabrics which have been washed with a detergent liquor and optionally rinsed in one or more inefficient rinse steps ("inefficient" in the sense that residual detergent and/or soil may be carried over with the fabrics) are pieced in the rinse solution with the diluted composition. Of course, the fabric softener composition may also be incorporated into the aqueous bath once the fabrics have been immersed therein. Following that step, agitation is applied to the fabrics in the rinse bath solution causing the suds to collapse, and residual soils and surfactant are to be removed. The fabrics can then be optionally wrung before drying.

The non-rinse rinse process may be performed manually a basin or bucket, in a non-automated washing machine, or in an automated washing machine. When hand washing is performed, the laundered fabrics are removed from the detergent liquor and wrung out. The fabric softener of the present invention is then added to fresh water and the fabrics are then, directly in case of the non-rinse process or after one or more optional inefficient rinse steps in case of the rinse process, rinsed in the water containing the composition according to the conventional rinsing habit. The fabrics are then dried using conventional means.

The fabric softener composition can be used to soften fabrics by treating the fabric with the composition. This can be done during the non-rinse and rinse process using a liquid fabric softener.

The following examples are given in order to provide a person skilled in the art with a sufficiently clear and complete explanation of the present invention, should not be considered as limiting of the essential aspects of its subject, as set out in the preceding portions of this description.

EXAMPLES

The first part of the Examples section refers to the preparation of the fabric softener active compositions according to the invention.

The second and third part of the Examples indicates analytical methods and physical properties methods, respectively, used to analyse the prepared fabric softener active compositions.

The fourth part of the Examples section presents some fundamental physical-chemical characteristics of the prepared fabric softener active compositions; content of residual amine, content of fatty acid ester, content of free fatty acid, content of fatty alcohol, content of solvent, dropping point, and melt viscosity.

The fifth part of the Examples refers to the preparation of the fabric softener compositions according to the invention, the determination of the initial viscosity of the aqueous dispersions and to the performance evaluation of their softening properties.

1. Preparation of the Fabric Softener Active Compositions According to the invention.

Selected examples correspond to the fabric softener active compositions based on tallow fatty acids.

Example 1

Esterification 603.0 grams (2.22 mol) of tallow fatty acid and 603.0 grams (2.22 mol) of hydrogenated tallow fatty acid were introduced in an inert atmosphere into a stainless steel reactor, and 400.4 grams (2.69 mol) of triethanolamine were added with stirring. The mixture was heated for at least 4 hours at 160-180° C. in order to remove water from the reaction. The final point of the reaction was monitored by an acid value assay, until the value was below 2 mg KOH/g.

A yellowish liquid product from the esterification step was obtained, consisting essentially of a mixture of unesterified fatty acids, mono-, di- and triesterified triethanolamine and unreacted triethanolamine.

Quaternization 46.8 grams (0.17 mol) of tallow fatty acid and 46.8 grams (0.17 mol) of hydrogenated tallow fatty acid were added with stirring to 1602.4 grams of the product from the esterification step (containing 3.0 mol of esteramine). Then, 359.1 grams (2.85 mol) of dimethyl sulphate were added with stirring at a temperature of 50-90° C. After four hours of digestion, the virtually complete absence of amine value was verified by acid/base assay. Finally, 85.6 grams of isopropanol were added to obtain a total of 2140.3 grams of the final product.

Example 2

Esterification 483.8 grams (1.78 mol) of tallow fatty acid and 483.8 grams (1.78 mol) of hydrogenated tallow fatty acid were introduced in an inert atmosphere into a stainless steel reactor, then 201.6 grams (1.35 mol) of triethanolamine and 22.4 grams (0.19 mol) of methyldiethanolamine were added with stirring together with 183.8 grams (0.68 mol) of stearyl alcohol. The mixture was heated for at least 4 hours at 160-180° C. in order to remove the water of the reaction. The final point of the reaction was monitored by an acid value assay, until the value was below 2 mg KOH/g.

A yellowish liquid product from the esterification step is obtained, consisting essentially of a mixture of unesterified fatty acids, mono-, di- and triesterified triethanolamine, mono- and diesterified methyldiethanolamine, esterified fatty alcohol and unreacted triethanolamine, methyldiethanolamine and fatty alcohol.

Quaternization 1354.1 grams of the product from the esterification step (containing 1.67 mol of esteramine) were reacted with 200.2 grams (1.59 mol) of dimethyl sulphate, which were added with stirring at a temperature of 50-90° C. After four hours of digestion, the virtually complete absence of amine value was verified by acid/base assay. Finally, 64.7 grams of isopropanol were added to obtain total of 1619.1 gram of the final product.

Example 3

Esterification 492.7 grams (1.81 mol) of tallow fatty acid and 492.7 grams (1.81 mol) of hydrogenated tallow fatty acid were introduced in an inert atmosphere into a stainless steel reactor, then 170.1 grams (1.14 mol) of triethanolamine and 42.5 grams (0.36 mol) of methyldiethanolamine were added with stirring together with 180.3 grams (0.68 mol) of stearyl alcohol. The mixture was heated for at least 4 hours at 160-180° C. in order to remove the water of the reaction. The final point of the reaction was monitored by an acid value assay, until the value was below 2 mg KOH/g.

A yellowish liquid product from the esterification step is obtained, consisting essentially of a mixture of unesterified fatty acids, mono-, di- and triesterified triethanolamine, mono- and diesterified methyldiethanolamine, esterified fatty alcohol, and unreacted triethanolamine, methyldiethanolamine and fatty alcohol.

Quaternization 1294.4 grams of the product from the esterification step (containing 1.54 mol of esteramine) were reacted with 184.4 grams (1.46 mol) of dimethyl sulphate, which were added with stirring at a temperature of 50-90° C. After four hours of digestion, the virtually complete absence of amine value was verified by acid/base assay. Finally, 61.6 grams of isopropanol were added to obtain, a total 1540.4 grams of the final product.

2. Analytical

Potentiometric Acid/Base Titrations

Content on amine salt and free fatty acid were determined by non-aqueous potentiometric titration with KOH. Samples were dissolved in 2-propanol.

Total amine value was determined by non-aqueous potentiometric titration with perchloric acid solution in glacial acetic acid.

Residual amine value, which corresponds to the non-quaternized amine fraction, was calculated as the sum of total amine value and amine salt.

All these varies e pressed as mg KOH per g.

GLC Analysis

Content of fatty acid fatty alcohol ester and free fatty alcohol were determined by GLC analysis, using an internal standard. Samples were dissolved in chloroform.

3. Physical Properties Methods

Dropping point was determined by the capillary method as the temperature at which the first drop falls or flows out of the standard cylindrical cup with a circular hole with a diameter of 2.8 mm in the bottom. Samples were melted and introduced in cup. They were left to solidify can 12-24 hours in a refrigerator at a low temperature (−20° C.) (an initial temperature of at least 5° C. below the expected dropping point is required). Samples were then subjected to a constant heating rate (1° C./min) to the point when they flowed through the hole, corresponding to the dropping point Melt viscosities were taken at 70° C. on a Rheometer Haake model RS600 at a shear rate of 5 s−1 using 60 mm serrated parallel plates with a plate distance of 0.8 mm.

4. Physical-Chemical Characteristics of the Prepared Fabric Softener Active Compositions.

Physical-chemical characteristics of the fabric softener active compositions, prepared as it has been described in the first part of the Examples section, are summarized in Table 1 below.

TABLE 1

|  | Examples | | |
| --- | --- | --- | --- |
| Physical-chemical property | 1 (comparative) | 2 | 3 |
| FA: Tallow/Hydrogenated tallow ratio | 50/50 | 50/50 | 50/50 |
| Residual amine value (mg KOH/g) | 13.2 | 8.3 | 7.8 |
| Ratio triethanolamine:methyldiethanolamine | — | 90:10 | 80:20 |
| (b) Fatty acid fatty alcohol ester (%) | — | 12.7 | 14.0 |
| (c) Free fatty acid (%) | 1.6 | 0.9 | 0.8 |
| (d) Free fatty alcohol (%) | — | 3.8 | 2.6 |
| (e) Isopropanol (%) | — | 4.0 | 4.0 |
| Dropping point (° C.) | 69.3 | 50.0 | 49.9 |
| Viscosity (cP) at 70° C. | 5997 | 210 | 189 |

Examples 2 and 3 correspond to fabric softener active compositions within the scope of the invention, and have dropping points below 60° C. which will allow the handling at molten state at maximum 70° C., ensuring a good chemical stability. In the same way, all fabric softener active compositions according to the invention show moderate viscosity values at 70° C., so that they can be easily pumped in the molten state.

In contrast, Example 1 (comparative) accounts for a fabric softener active composition not within the scope of the invention. It has a dropping point above 60° C., which would demand a handling temperature overcoming 70° C., compromising the chemical stability of the product. Accordingly, the fabric softener active compositions within the scope of the invention have suitable viscosity at low content or in the absence of flammable solvents and at the same time.

5. Preparation of the fabric softener compositions according to the invention and performance evaluation of their softening properties.

Fabric softener compositions were made by dispersing fabric softener active compositions into water.

Aqueous dispersions shown in Table 2 contain 4.5% of fabric softener active compositions and 0.1% active of a thickening polymer (i.e. FLOSOFT 222 manufactured by SNF).

The dispersion process consists of heating deionized water at 60° C. in a jacketed glass reactor, adding the thickening polymer while stirring until complete incorporation, adding the fabric softener active composition of interest in the molten state (heated 5 to 10° C. above the melting point) and homogenizing the dispersion at a rate of 150 rpm during 20 min. The aqueous dispersion is finally cooled down up to 25-30° C., at rate of 1.0° C./min, maintaining the agitation at 150 rpm.

Initial viscosity of the aqueous dispersions was determined at 24 h after preparation, with a Brookfield viscosimeter model LV, using a spindle number 2 at 66 rpm.

Softening performance of fabric softener compositions determined by means of a sensorial test carried out by a panel of experts using pieces of terry cotton towel treated with the corresponding aqueous dispersions of the fabric softener active compositions.

Fabric treatment consists of a consecutive sequence of washing and softening steps, carried out in hard water of 20° HF. Previously scoured terry cotton towels were washed at 40° C. with a heavy duty powder detergent (at a dosage of 2.7% on weight fabric), rinsed twice and spinning dried. Wet towels were treated for 10 minutes at 25° C. with the corresponding aqueous dispersions diluted in water to provide a dosage of 0.12% fabric softener active composition on weight fabric, for a bath ratio of 1/10. Treated cotton towels were finally spun dried and let dry by hanging, and left still for 24 hours under controlled atmospheric conditions (60% HR and 20° C.).

Softening effect was determined by comparison in pairs, by 12 panelists, against standard products of equivalent hydrogenation degree (comparative examples C1 and C2). Results are indicated in Table 2. The comparative evaluation was made according to the following criteria:

+3: much softer than the reference
+2: softer than the reference
+1: slightly softer than the reference
0 as soft as the reference
−1: slightly harder than the reference
−2: harder than the reference
−3: much harder than the reference

TABLE 2

| Fabric softener active composition | 2 | 3 | C1 |
| --- | --- | --- | --- |
| Initial viscosity at 20° C. (cP) | 140 | 205 | 115 |
| Softening effect | +2 | +3 | — |
| compared to | C1 | C1 | — |

C1: TETRANYL® L2-90 Available from Kao Corporation, Ester Quat with a Tallow/Hydrogenated Tallow Ratio 50/50

It can be seen that all fabric softener active compositions within the scope of the invention provide acceptable viscosity values and higher softening effects than the fabric softener active compositions of the corresponding comparative examples.

The invention claimed is:

1. A fabric softener active composition comprising:
   a component (a), said component comprising a mixture of at least a quaternary ester ammonium compound of formula (I) and at least a quaternary ester ammonium compound of formula (II):

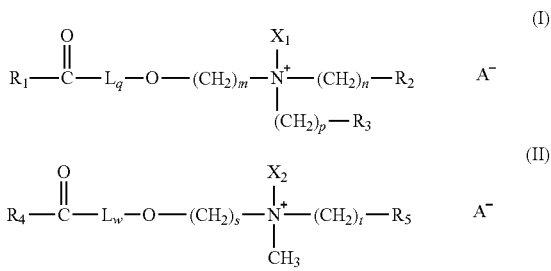

wherein in formula (I):
   $X_1$ represents a hydroxyalkyl group containing 1 to 4 carbon atoms, an alkyl group containing 1 to 4 carbon atoms or an alkyl group containing one aromatic group;
   $R_1$ is a linear or branched alkyl group containing 5 to 23 carbon atoms or a linear alkenyl group containing 5 to 23 carbon atoms and 1 to 3 double bonds;
   $R_2$ and $R_3$ each independently represent —OH or —O-L-C(O)—$R_1$;
   L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26:

m, n and p each independently represent a number within the range from 1 to 4, q represents a number within the range from 0 to 26 and A represents an anion;

and wherein in formula (II):

$X_2$ represents a hydroxyalkyl group containing 1 to 4 carbon atoms, an alkyl group containing 1 to 4 carbon atoms or an alkyl group containing one aromatic group;

$R_4$ is a linear or branched alkyl group containing 5 to 23 carbon atoms or a linear alkenyl group containing 5 to 23 carbon atoms and 1 to 3 double bonds;

$R_5$ represents a —H, OH or —O-Lw-C(O)—$R_4$;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and A represents an anion;

a component (b), said component being a fatty acid ester or a mixture of fatty acid esters, wherein the component (b) content is in the range from 5 to 60% wt. based on the total weight of the fabric softener active composition;

a component (c), said component being a fatty acid or a mixture of fatty acids, wherein the component (c) content is in the range from 0 to 15% wt. based on the total weight of the fabric softener active composition;

a component (d), said component being a fatty alcohol or a mixture of fatty alcohols, wherein the component (d) content is higher than 0% wt. and lower than 20% wt. based on the total weight of the fabric softener active composition; and optionally, further comprising a component (e), said component being a solvent, wherein the content of component (e), if resent is higher than 0% wt. and lower than 8% wt. based on the total weight of the fabric softener active composition.

2. The fabric softener active composition according to claim 1, wherein the mixture of at least a quaternary ester ammonium compound of formula (I) and at least a quaternary ester ammonium compound of formula (II) comprises at least one or more quaternary mono-, di- or tri-ester ammonium compounds of formula (I1), (I2), (I3), and at least one or more quaternary mono or di-ester ammonium compounds of formula (II1), (II2):

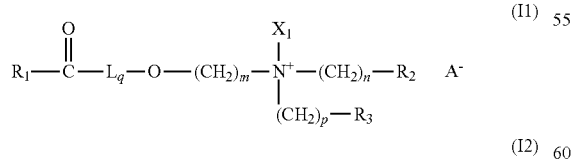

(I1)

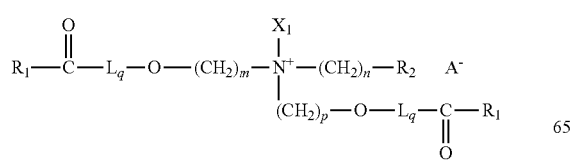

(I2)

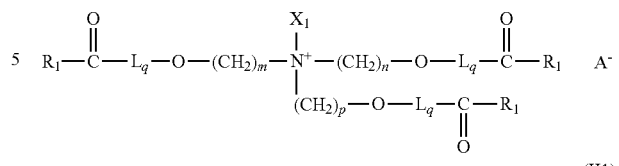

(I3)

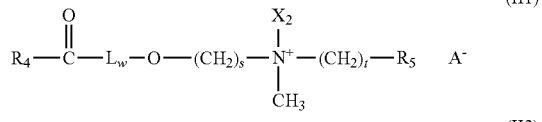

(II1)

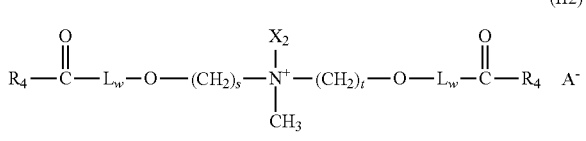

(II2)

wherein in formulae (I1), (I2), (I3)

$R_2$ and $R_3$ each independently represent -OH;

$X_1$ represents a hydroxyalkyl group containing 1 to 4 carbon atoms, an alkyl group containing 1 to 4 carbon atoms or an alkyl group containing one aromatic group;

$R_1$ is a linear or branched alkyl containing 5 to 23 carbon atoms or a linear alkenyl group containing 5 to 23 carbon atoms and from 1 to 3 double bonds, in formulae I1, I2 and I3 each $R_1$ can independently represent the same or different linear or branched alkyl chain;

$A^-$ represents an anion;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6, and the sum of a+b represents the average alkoxylation degree which corresponds to a number from 0 to 26;

m, n, p each independently represents a number within the range from 1 to 4, q represents a number within the range from 0 to 26;

and wherein in formulae (II1), (II2)

$X_2$ represents a hydroxyalkyl group containing 1 to 4 carbon atoms, an alkyl group containing 1 to 4 carbon atoms or an alkyl group containing one aromatic group;

$R_4$ is a linear or branched alkyl group containing 5 to 23 carbon atoms or a linear alkenyl group containing 5 to 23 carbon atoms and 1 to 3 double bonds;

$R_5$ represents —OH;

L represents a —(OCH$_2$CH$_2$)$_a$—(OCHR$_6$CH$_2$)$_b$— group, wherein $R_6$ represents an alkyl group containing 1 to 4 carbon atoms, a represents a number within the range of 0 to 20, b represents a number within the range of 0 to 6 and the sum of a+b represents the average alkoxylation degree which corresponds to a number within the range from 0 to 26;

s and t each independently represent a number within the range from 1 to 4, w represents a number within the range from 0 to 26 and $A^-$ represents an anion.

3. The fabric softener active composition according to claim 1, characterized in that in formula (I), m, n and p represent number 2.

4. The fabric softener active composition according to claim 1, characterized in that in formula (II), s and t represent number 2.

5. The fabric softener active composition according to claim 1, wherein either the component (b) is a a fatty acid ester or a mixture of fatty acid esters derived from a $C_{12}$-$C_{18}$ fatty alcohol or a mixture of $C_{12}$-$C_{18}$ fatty alcohols.

6. The fabric softener active composition according to claim 1, wherein the component (a), the component (b), the component (c) are derived from the same fatty acid or mixture of fatty acids.

7. The fabric softener active composition according to claim 1, wherein the component (d) is a $C_{12}$-$C_{18}$ fatty alcohol or a mixture of $C_{12}$-$C_{18}$ fatty alcohols.

8. A method for producing a fabric softener active composition as defined in claim 1 comprising:
  i) an esterfication step, wherein a fatty acid, a methyl ester or a triglyceride thereof is reacted with a mixture of alkanolamines to obtain a mixture containing an esteramine; and
  ii) a quaternization step, wherein the mixture obtained after the esterification step is reacted with an alkylating agent.

9. The method according to claim 8, wherein the mixture of akanolamines comprises at least a trialkanolamine and at least an alkyldialkanolamine and/or a dialkylalkanolamine.

10. The method according to claim 8, wherein the component (b) present in the fabric softener active composition is intentionally added and/or generated in situ in the esterification step, after the esterification step, in the quaternization step or after the quaternization step.

11. The method according to claim 8, wherein the component (b) is generated in situ by reaction with component (d) which is added in the esterification step, after the esterification step, in the quaternization step or after the quaternization step.

12. The method according to claim 8, wherein component (c) present in the fabric softener active composition is intentionally added in the esterification step, after the esterification step, in the quaternization step or after the quaternization step.

13. A fabric softener composition comprising a fabric softener active composition as defined in claim 1, further comprising at least water, wherein the fabric softener active composition is present in an amount from 1 to 30% wt. based on the total weight of the fabric softener composition, and optionally comprising the further components:
  from 0 to 2% of an electrolyte concentration aid; and/or
  from 0.01 to 3% of a thickening polymer; and/or
  from 0.01 to 5% of a perfume.

14. Use of the fabric softener composition as defined in claim 13 to soften and condition fabrics, by contacting the fabrics with the fabric softener composition at one or more points during a laundering process, and allowing the fabrics to dry or mechanically tumble-drying the fabrics.

15. A method for producing a fabric softener composition, comprising the steps:
  i) adding the fabric softener active composition as defined in claim 1 in a molten state to water, wherein the fabric softener active composition is present in an amount of from 1 to 30% by weight, based on the total weight of the fabric softener composition;
  ii) stirring to obtain a homogeneous dispersion;
  iii) cooling down;
  iv) optionally mixing in further components, of from 0 to 2% of an electrolyte concentration aid; and/or from 0.01 to 3% of a thickening polymer; and/or from 0.01 to 5% of a perfume wherein the further components can be added to the water before or after any one of steps i) to iii).

\* \* \* \* \*